(12) United States Patent
Shin et al.

(10) Patent No.: US 10,413,893 B2
(45) Date of Patent: Sep. 17, 2019

US010413893B2

(54) DEACTIVATOR AND METHOD FOR DECREASING BY-PRODUCTS IN OLEFIN OLIGOMERIZATION USING THE SAME

(71) Applicant: LG CHEM, LTD., Seoul (KR)

(72) Inventors: Eun Ji Shin, Daejeon (KR); Yong Ho Lee, Daejeon (KR); Seul Ki Im, Daejeon (KR); Ki Soo Lee, Daejeon (KR); Jin Young Park, Daejeon (KR); Seok Pil Sa, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/517,758

(22) PCT Filed: Feb. 2, 2016

(86) PCT No.: PCT/KR2016/001142
§ 371 (c)(1),
(2) Date: Apr. 7, 2017

(87) PCT Pub. No.: WO2016/129845
PCT Pub. Date: Aug. 18, 2016

(65) Prior Publication Data
US 2017/0305811 A1 Oct. 26, 2017

(30) Foreign Application Priority Data

Feb. 12, 2015 (KR) .................. 10-2015-0021784
Jan. 21, 2016 (KR) .................. 10-2016-0007421

(51) Int. Cl.
| | | |
|---|---|---|
| *C07C 2/02* | (2006.01) | |
| *C07C 2/04* | (2006.01) | |
| *C07C 2/24* | (2006.01) | |
| *C07C 2/26* | (2006.01) | |
| *B01J 31/24* | (2006.01) | |
| *B01J 31/02* | (2006.01) | |
| *B01J 31/04* | (2006.01) | |
| *B01J 31/14* | (2006.01) | |
| *C07C 2/32* | (2006.01) | |
| *C08F 210/16* | (2006.01) | |
| *C08F 2/40* | (2006.01) | |
| *C08F 4/69* | (2006.01) | |
| *C08F 10/00* | (2006.01) | |

(Continued)

(52) U.S. Cl.
CPC ....... *B01J 31/2409* (2013.01); *B01J 31/0267* (2013.01); *B01J 31/04* (2013.01); *B01J 31/143* (2013.01); *B01J 31/187* (2013.01); *B01J 35/0006* (2013.01); *B01J 37/04* (2013.01); *C07C 2/24* (2013.01); *C07C 2/32* (2013.01); *C07F 9/505* (2013.01); *C07F 9/5022* (2013.01); *C08F 2/40* (2013.01); *C08F 4/69* (2013.01); *C08F 10/00* (2013.01); *C08F 10/02* (2013.01); *C08F 210/16* (2013.01); *C08K 5/00* (2013.01); *C08K 5/05* (2013.01); *C08K 5/17* (2013.01); *B01J 2231/12* (2013.01); *B01J 2231/20* (2013.01); *B01J 2523/67* (2013.01); *B01J 2531/004* (2013.01); *B01J 2531/31* (2013.01); *B01J 2531/62* (2013.01); *C07C 2523/26* (2013.01); *C07C 2531/04* (2013.01); *C07C 2531/14* (2013.01); *C07C 2531/18* (2013.01); *C07C 2531/22* (2013.01); *C07C 2531/24* (2013.01)

(58) Field of Classification Search
CPC .................................. C07C 2/02; C07C 2/24
USPC .................................................. 585/510, 520
See application file for complete search history.

(56) References Cited

U.S. PATENT DOCUMENTS

| 3,720,616 A | * 3/1973 | Randell ................ C07D 249/18 |
| | | 106/10 |
| 3,962,196 A | 6/1976 | Weimer et al. |

(Continued)

FOREIGN PATENT DOCUMENTS

| BE | 684587 A | 1/1967 |
| CN | 87103140 A | 11/1987 |

(Continued)

OTHER PUBLICATIONS

Bouzid, et al.: "Improving Impact Poly(propylene) Morphology and Production: Selective Poisoning of Catalyst Surface Sites and the Use of Antistatic Agents", XP 55433495A, Macromolecular Chemistry and Physics, vol. 207, No. 1, Jan. 3, 2006, pp. 13-19.

(Continued)

*Primary Examiner* — Youngsul Jeong
(74) *Attorney, Agent, or Firm* — Lerner, David, Littenberg, Krumholz & Mentlik, LLP

(57) ABSTRACT

The method for oligomerizing olefin according to the present disclosure is a method for oligomerizing olefin using an oligomerization catalyst system and includes deteriorating the activity of the oligomerization catalyst system by injecting a deactivator in a latter part of a multimerization reaction of olefin. The deactivator may include an additive for polymer containing at least one functional group selected from the group consisting of a hydroxyl group, an amine group and an amide group. According to the oligomerizing method, the isomer of 1-hexene and/or 1-octene and alpha-olefins with $C_{10}$ to $C_{40}$ may be decreased via the restraint of the additional side reaction of a product. Since the deactivator is an additive for enhancing the physical properties of a polymer, a separating process thereof is not required, thereby improving economic feasibility and productivity.

12 Claims, No Drawings

(51) Int. Cl.
  *C08K 5/05* (2006.01)
  *B01J 31/18* (2006.01)
  *C07F 9/50* (2006.01)
  *C08K 5/00* (2006.01)
  *C08K 5/17* (2006.01)
  *B01J 35/00* (2006.01)
  *B01J 37/04* (2006.01)
  *C08F 10/02* (2006.01)

(56) References Cited

U.S. PATENT DOCUMENTS

| | | | |
|---|---|---|---|
| 4,551,509 A | 11/1985 | Takayuki et al. | |
| 4,650,841 A | 3/1987 | Levresse et al. | |
| 4,803,259 A * | 2/1989 | Zboril | C08F 6/02 524/249 |
| 5,196,630 A * | 3/1993 | Agrawal | C08F 6/02 585/525 |
| 6,180,730 B1 * | 1/2001 | Sibtain | C08F 6/02 526/128 |
| 2003/0166456 A1 | 9/2003 | Wass | |
| 2004/0143147 A1 * | 7/2004 | Ittel | C07C 2/32 585/521 |
| 2004/0236040 A1 | 11/2004 | Mihan et al. | |
| 2005/0020788 A1 | 1/2005 | Wass | |
| 2005/0119516 A1 | 6/2005 | Dixon et al. | |
| 2006/0025640 A1 * | 2/2006 | Karjala | C08F 210/16 585/17 |
| 2006/0229480 A1 | 10/2006 | Blann et al. | |
| 2007/0264171 A1 * | 11/2007 | Herrmann | B01J 8/0055 422/136 |
| 2008/0207857 A1 | 8/2008 | Small et al. | |
| 2010/0113257 A1 | 5/2010 | Kreischer et al. | |
| 2010/0113851 A1 | 5/2010 | Kreischer et al. | |
| 2010/0113852 A1 | 5/2010 | Sydora | |
| 2010/0216958 A1 * | 8/2010 | Peters | C07D 333/48 526/258 |
| 2010/0274065 A1 * | 10/2010 | Sydora | B01J 31/122 585/513 |
| 2011/0046429 A1 | 2/2011 | Aliyev et al. | |
| 2011/0184137 A1 | 7/2011 | Qin et al. | |
| 2012/0172645 A1 * | 7/2012 | Sydora | B01J 31/143 585/511 |
| 2012/0184692 A1 | 7/2012 | Fritz et al. | |
| 2013/0253126 A1 * | 9/2013 | Ewart | C08L 23/06 524/528 |
| 2014/0072820 A1 | 3/2014 | Chen | |
| 2015/0148502 A1 | 5/2015 | Christianson et al. | |
| 2015/0284303 A1 | 10/2015 | Zoricak et al. | |
| 2015/0291711 A1 | 10/2015 | Qin et al. | |
| 2016/0053031 A1 | 2/2016 | Christianson et al. | |

FOREIGN PATENT DOCUMENTS

| | | |
|---|---|---|
| CN | 1516707 A | 7/2004 |
| CN | 103285926 A | 9/2013 |
| CN | 103339186 A | 10/2013 |
| EP | 0102860 A1 | 3/1984 |
| EP | 0811638 A2 | 12/1997 |
| EP | 2287142 A1 | 2/2011 |
| FR | 2289523 A1 | 5/1976 |
| FR | 2538397 A1 | 6/1984 |
| JP | S51-032156 B1 | 9/1976 |
| JP | 2004502527 A | 1/2004 |
| JP | 2005513115 A | 5/2005 |
| JP | 2006517528 A | 7/2006 |
| JP | 2007119383 A | 5/2007 |
| JP | 2011510939 A | 4/2011 |
| JP | 2013500240 A | 1/2013 |
| JP | 2014521756 A | 8/2014 |
| KR | 10-2010-0113534 A | 10/2010 |
| KR | 10-2011-0081940 A | 7/2011 |
| KR | 10-2012-0050963 A | 5/2012 |
| KR | 10-2013-0142151 A | 12/2013 |
| WO | 95/07943 A1 | 3/1995 |
| WO | 03/042253 A1 | 5/2003 |
| WO | 03/053891 A1 | 7/2003 |
| WO | 2004/043887 A2 | 5/2004 |
| WO | 2009/155170 A2 | 12/2009 |
| WO | 2012/155022 A1 | 11/2012 |
| WO | 2013/067620 A1 | 5/2013 |
| WO | 2014/055868 A1 | 4/2014 |
| WO | 2014/094114 A1 | 6/2014 |

OTHER PUBLICATIONS

Chinese Search Report for CN2016800033163 dated Mar. 26, 2019.

* cited by examiner

DEACTIVATOR AND METHOD FOR DECREASING BY-PRODUCTS IN OLEFIN OLIGOMERIZATION USING THE SAME

TECHNICAL FIELD

Cross-Reference to Related Applications

This application claims the benefits of priority based on Korean Patent Application Nos. 10-2015-0021784, filed on Feb. 12, 2015, and 10-2016-0007421, filed on Jan. 21, 2016, and the entire contents of which are hereby incorporated by reference.

TECHNICAL FIELD

The present invention relates to a method for oligomerizing olefin, and a method for decreasing by-products in the olefin oligomerization by deteriorating the activity of an oligomerization catalyst system using a deactivator.

BACKGROUND ART

Linear alpha-olefins, which are important materials used as comonomers, cleaners, lubricants, plasticizers and the like, are commercially widely used, and particularly, 1-hexene and 1-octene are used a lot as comonomers for controlling the density of polyethylene when preparing linear low-density polyethylene (LLDPE).

In the preparation process of common LLDPE, copolymerization of alpha-olefins, for example, 1-hexene, 1-octene, etc. with ethylene is performed to control density by forming branches on the polymer backbone.

Accordingly, in the preparation of LLDPE having a high comonomer content, the comonomer is a costly part. To resolve the drawback, various methods have been conducted.

In addition, the application field or the market size of alpha-olefins is dependent on the kind thereof, and technique on selective production of a specific olefin is commercially very important. Recently, research on chromium catalysts for preparing 1-hexene or 1-octene with high selectivity via selective ethylene oligomerization has been actively conducted.

Conventional commercial preparation methods of 1-hexene or 1-octene include the shell higher olefin process (SHOP) of Shell Chemicals, the Ziegler process of Chevron Philips chemical, etc. Through the methods, alpha-olefins having a wide distribution of $C_4$-$C_{20}$ may be obtained.

Meanwhile, research on the deactivation technique of an oligomerization catalyst system used during preparing has been continuously conducted. If the oligomerization catalyst is not deactivated, alpha-olefins produced may be isomerized during the subsequent separation process. Therefore, a deactivator for deteriorating or removing the activity of the oligomerization catalyst system is required.

Conventionally, long chain alcohols for example, decanol, etc. were used so as not to inhibit the separation of an alpha-olefin product, however the materials might become a contaminating material in a product, and a separating process of the decanol was essential.

Accordingly, a deactivating technique of an oligomerization catalyst system which may effectively prevent a side reaction during the separating process of the alpha-olefins thus produced and decrease costs and equipments required for the separation of a deactivator, is required.

DISCLOSURE OF THE INVENTION

Technical Problem

In the present disclosure, provided is a method for oligomerizing olefin, by which a side reaction during separating a product may be restrained, the production of by-products may be deteriorated, and the separation of a deactivator from the product may not be necessary, through decreasing the activity of an oligomerization catalyst system using a deactivator which is also an additive for enhancing the physical properties of a polymer.

Technical Solution

According to an aspect of the present invention, there is provided a method for oligomerizing olefin using an oligomerization catalyst system, including injecting a deactivator in a latter part of a multimerization reaction of olefin to deteriorate activity of the oligomerization catalyst system.

In an embodiment, the method may further include separating an alpha-olefin product and a polymer resin product after deteriorating the activity of the oligomerization catalyst system, and the polymer resin product may include polyethylene and the deactivator.

In an embodiment, a molar ratio of the oligomerization catalyst system and the deactivator may be from 1:1 to 1:100.

In an embodiment, the deactivator may include an additive for polymer including at least one functional group selected from the group consisting of a hydroxyl group, an amine group and an amide group.

In an embodiment, the additive for polymer may include at least one selected from the group consisting of an antistatic agent, an antioxidant, a lubricant, a stabilizer, a light stabilizer and a phase transfer catalyst.

In an embodiment, the antistatic agent may include at least one selected from the group consisting of bis(2-hydroxyethyl)pentadecylamine (Atmer 163), an ethoxylated fatty amine having 12 to 18 carbon atoms, glycerol monostearate, erucamide, stearamide, oleamide and benenamide.

In an embodiment, the antioxidant may include a phenol-based antioxidant, and the phenol-based antioxidant may include butylated hydroxytoluene (BHT).

In an embodiment, the lubricant may include at least one selected from the group consisting of erucamide, stearamide, oleamide, benenamide, an ethoxylated fatty amine having 12 to 18 carbon atoms and glycerol monostearate.

In an embodiment, the stabilizer may include triisopropanolamine (TIPA), quadrol(N,N,N,N-tetrakis(2-hydroxypropyl)-ethylenediamine) or a mixture thereof.

In an embodiment, the light stabilizer is an additive for decreasing or blocking the discoloration or the loss of mechanical properties due to the decomposition of a resin by light such as ultraviolet rays, and may include, for example, a benzophenone-based compound, a benzotriazole-based compound or a mixture thereof. The phase transfer catalyst may include tricaprylmethylammonium chloride (Aliquat 336).

In an embodiment, the oligomerization catalyst system may include a diphosphine-based ligand compound; a transition metal compound; and a co-catalyst.

In an embodiment, the transition metal compound may include an organic chromium compound, and the organic chromium compound may include at least one selected from the group consisting of chromium(III) acetyl acetonate, trichloro chromium tris tetrahydrofuran, chromium(III)-2- ethylhexanoate, chromium(III) tris (2,2,6,6-tetramethyl-3,5-heptanedionate), chromium(III) benzoyl acetonate, chromium(III) hexafluoro-2,4-pentanedionate and chromium(III) acetate hydroxide.

In an embodiment, the diphosphine-based ligand compound may include a compound represented by the following Formula 1 or 2.

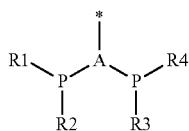

[Formula 1]

In Formula 1, A is N, As or Sb, R1 to R4 are each independently aryl having 6 to 20 carbon atoms or alkylaryl having 7 to 20 carbon atoms, and is a linker connecting at least two diphosphine moieties.

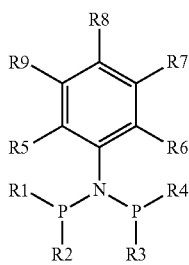

[Formula 2]

In Formula 2, R1 to R4 are the same as defined in Formula 1, and R5 is alkyl having 1 to 20 carbon atoms.

In the case that R5 is methyl, R6 is a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 is alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 are each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

In an embodiment, the linker in Formula 1 may be combined with at least one group selected from the group consisting of an aliphatic group having 1 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a heteroaromatic group having 6 to 20 carbon atoms.

According to another aspect of the present invention, there is provided a deactivator for deteriorating activity of an oligomerization catalyst system used for a multimerization reaction of olefin, wherein the deactivator includes an additive for polymer containing at least one functional group selected from the group consisting of a hydroxyl group, an amine group and an amide group.

In an embodiment, the additive for polymer may include at least one selected from the group consisting of an antistatic agent, an antioxidant, a lubricant, a light stabilizer and a phase transfer catalyst.

Advantageous Effects

In the method for oligomerizing olefin according to the present disclosure, a deactivator containing at least one functional group selected from the group consisting of a hydroxyl group, an amine group and an amide group is used, and the activity of an oligomerization catalyst system may be effectively deteriorated, the isomer of 1-hexene and/or 1-octene may be decreased by restraining the additional isomerization reaction of a product, and the alpha-olefins of $C_{10}$ to $C_{40}$ may be decreased by restraining the additional multimerization reaction of a product.

Further, economic feasibilities and productivity may be improved without performing a separating process of a deactivator, by using a deactivator which is also used as an additive for enhancing the physical properties of a polymer.

MODE FOR CARRYING OUT THE INVENTION

Hereinafter, the present invention will be described in detail to assist the understanding of the present invention. The terms or words used in the present disclosure or claims should not be defined or interpreted in common or dictionary meaning, but should be interpreted as having a meaning that is consistent with their meaning in technical spirit of the present invention on the basis that the inventors may appropriately define the concept of the terms to explain the invention by their best way.

The terminology used herein is for the purpose of describing particular example embodiments only and is not intended to limit the present inventive concept. As used herein, the singular forms are intended to include the plural forms as well, unless the context clearly indicates otherwise.

It will be further understood that the terms "comprises", "comprising", etc. when used in this specification, specify the presence of stated features, numerals, steps, elements or the combination thereof, but do not preclude the presence or addition of one or more other features, numerals, steps, elements or the combination thereof.

In the present disclosure throughout, the terms "catalyst system" or "catalyst composition" means a state obtainable as a catalyst composition having activity by adding three components including a transition metal source, a ligand compound and a co-catalyst, or alternatively, two components having a transition metal compound and a co-catalyst simultaneously or in an optional order. The three components or the two components of the catalyst system may be added in the presence or non-presence of a solvent and a monomer, and the three terms may interchangeably be used.

The term "oligomerization" used in the present disclosure means the oligomerization of olefin. According to the number of the olefin, trimerization, or tetramerization may be referred to, and the general term thereof is multimerization. Particularly, in the present disclosure, the oligomerization means the selective preparation of 1-hexene and 1-octene which are main comonomers of LLDPE from ethylene.

In the present disclosure, a hydrocarbyl group means all compounds composed of only carbon and hydrogen, for example, alkyl, aryl, alkenyl, cycloalkyl, etc., and the hydrocarbyl group may mean both a linear chain and a branched chain unless otherwise referred to and may mean both unsubstituted and substituted type. For example, the alkyl having 1 to 20 carbon atoms may mean methyl, ethyl, propyl, isopropyl, butyl, isobutyl, pentyl, isopentyl, neopentyl, etc., and the aryl having 6 to 20 carbon atoms may mean, for example, phenyl, naphthyl, anthracenyl, etc., without limitation.

In the present disclosure, an alkylaryl group means aryl having at least one alkyl group as a substituent, and an arylalkyl group means alkyl having at least one aryl group as a substituent.

In the present disclosure, a heteroatom means N, O, S or P, and the heterohydrocarbyl may mean hydrocarbyl including at least one heteroatom. That is, the heteroalkyl may mean an alkyl of which one carbon is substituted with a heteroatom or may mean an alkyl including a heteroatom as a substituent. Heteroaryl group may mean an aromatic ring of which one carbon is substituted with a heteroatom such as pyridyl. In addition, the same may go for heteroarylakyl, heteroalkylaryl, heteroalkenylaryl, etc.

In the heterohydrocarbyl group, a linking point for functionalization is carbon, however, in "heteryl group" such as "hydrocarboheteryl group", "organoheteryl group", "heteryl group thereof", etc., the linking point for functionalization is a heteroatom.

Method for Oligomerizing Olefin

Activity Deterioration of Oligomerization Catalyst System by Injecting Deactivator A method for oligomerizing olefin according to an embodiment of the present invention includes a step of injecting a deactivator in a latter part of a tetramerization reaction of oligomer to deteriorate the activity of an oligomerization catalyst system.

The step of deteriorating the activity of the oligomerization catalyst system may be a step of deteriorating the activity of the oligomerization catalyst system by injecting a deactivator to a product mixture drained from a multimerization reactor after performing the multimerization reaction of olefin and prior to separating the product mixture into alpha-olefins and other by-products.

The deterioration of the oligomerization catalyst system via the deactivator may mean that the activation point of the oligomerization catalyst system may be partially or wholly removed, and after the deterioration of the activity of the catalyst system, common roles such as the activation of an oligomerization reaction and/or an isomerization reaction may become difficult.

By injecting the deactivator, the production of an isomer due to the isomerization of alpha-olefins, which may be generated due to the maintenance of the activity of the catalyst, or the generation of alpha-olefins of $C_{10}$ to $C_{40}$ due to multimerization, in a mixture separating process which may be performed in high temperature and/or high pressure environment, may be prevented.

For the injection of the deactivator, a separate supplying pipe line may be installed on a pipe line for draining a production mixture in a multimerization reactor, or a separate apparatus for mixing the production mixture and the deactivator may be installed by installing a tank, however the injection method of the deactivator according to the present disclosure is not limited thereto. In the case that the deactivator is injected via the separate supplying pipe line, in order to secure sufficient contacting time of the catalyst system and the deactivator for deteriorating catalyst activity, the separate supplying pipe line may preferably be installed near the multimerization reactor in a separating process, for example, a distillation column.

The molar ratio of the oligomerization catalyst system and the deactivator may be from 1:1 to 1:100. In the case that the deactivator is injected less than one time of the oligomerization catalyst system, the activity of the oligomerization catalyst system may not be sufficiently deteriorated, and the production amount of by-products may increase. In the case that the deactivator is injected greater than 100 times of the oligomerization catalyst system, since the deactivator does not act as a contaminating source in a product, there's no concern to induce big problems, however subsidiary problems such as economic disadvantage may occur.

The deactivator may be an additive for polymer containing at least one functional group selected from the group consisting of a hydroxyl group, an amine group and an amide group. The deactivator includes the additive for polymer and may include other solvents, a small amount of a certain material for deteriorating the activity of the catalyst other than the additive for polymer.

The additive for polymer which is the main component of the deactivator may be a compound containing each of the hydroxyl group, the amine group or the amide group solely, a compound containing both the hydroxyl group and the amine group at the same time, a compound containing both the hydroxyl group and the amide group at the same time, a compound containing both the amine group and the amide group at the same time, or a compound containing the hydroxyl group, the amine group and the amide group at the same time.

The hydroxyl group is a functional group represented by —OH, the amine group includes a primary amine represented by —NH$_2$, a secondary amine represented by —NHR, or a tertiary amine represented by —NR$_2$, and the amide group is a functional group represented by —CONH$_2$, —CONHR or —CONR$_2$. However, due to specific causes inherent in a product or a solvent, or due to the original state of a specific polymer additive, the hydroxyl group may mean an ionized functional group of —OH$_2^+$, the amine group may mean an ionized ammonium group of —NH$_3$, —NH$_2$R$^+$, —NHR$_2^+$ or —NR$_3^+$, and the amide group may mean an ionized functional group of —CONH$_3^+$, —CONH$_2$R$^+$, —CONHR$_2^+$ or —CONR$_3^+$.

The deactivator may include an additive for polymer used as a compound added to enhance the mechanical, chemical or electrical properties of a polymer. The additive for polymer may be any material including at least one of the above-mentioned functional groups without limitation and may be applied in a step of deteriorating the activity of the catalyst according to the present disclosure. For example, an additive for polymer such as an antistatic agent, an antioxidant, a lubricant, a stabilizer, a light stabilizer, a phase transfer catalyst, and a mixture thereof may be applied.

Particularly, the antistatic agent is an additive for polymer for decreasing or removing static electricity generated at the surface of a resin product and may include, for example, ethoxylated fatty amine having 12 to 18 carbon atoms, bis(2-hydroxyethyl)pentadecylamine (Atmer 163), glycerol monostearate, erucamide, stearamide, oleamide, benenamide, etc.

The antioxidant may preferably include a phenol-based antioxidant and is an additive for polymer added to prevent the decomposition of a resin and the loss of the inherent physical properties of the resin by deteriorating or blocking a chemical reaction between a resin product and oxygen. For example, a phenol-based compound such as butylated hydroxytoluene (BHT), or an aromatic amine compound may be applied.

In addition, the lubricant is an additive for lubricating the surface of a contacting metal during performing processing, molding, or extruding a resin for easy flowing. For example, erucamide, stearamide, oleamide, benenamide, ethoxylated fatty amide having 12 to 18 carbon atoms, glycerol monostearate, etc. may be applied.

The stabilizer is an additive preventing the decomposition of a polymer, and for example, triisopropanolamine (TIPA), quadrol(N,N,N,N-tetrakis(2-hydroxypropyl)-ethylenediamine), or a mixture thereof may be applied.

The light stabilizer is an additive for decreasing or blocking the discoloration or the loss of mechanical properties of a resin due to the decomposition of the resin by light such as ultraviolet rays. For example, a benzophenone-based compound such as benzophenone, or a benzotriazole-based compound may be applied. In addition, the phase transfer catalyst generally means a catalyst promoting a reaction through moving between two phases (aqueous phase and oily phase) and transport reactants from one phase to the other phase, and may include a liphophilic quaternary ammonium salt, a large ring shaped polyether, etc. In general, a quaternary ammonium salt such as tricaprylymethylammonium chloride (Aliquat 336) may be applied.

As described above, the deactivator may be an additive for polymer which may be added a polymer resin to improve the physical properties. After separating alpha-olefins such as 1-hexene and/or 1-octene, the deactivator remaining in the polymer resin of polyolefin containing polyethylene, etc. which may be another product, may not affect the deterioration of the quality thereof, but rather improve the physical properties thereof.

Therefore, after injecting the deactivator and deteriorating the activity of the catalyst, a separating process of the deactivator is not required, and one or more steps may be omitted to improve productivity and subsidiary advantages including economic feasibility may be attained.

When the additive for polymer is used as the deactivator for deteriorating the activity of the oligomerization catalyst system used in an olefin oligomerization method, a separating process is not required, the generation of a side reaction during separating a product may be markedly decreased. Accordingly, the contents of the isomer of 1-hexene and/or 1-octene or the contents of $C_{10}$ to $C_{40}$ alpha-olefins in a final product including 1-hexene and 1-octene may be decreased.

The percentage of the isomer of 1-octene in a total amount is not large, and decreasing degree thereof due to the injection of the deactivator may be trivial. However, in the olefin oligomerization, the percentage of the isomer of 1-hexene in a final product is basically significant, and the decreasing effect via the injection of the deactivator according to the present disclosure may be significant. In addition, the amount of $C_{10}$ to $C_{40}$ alpha-olefins such as $C_{12}$ alpha-olefins or $C_{16}$ alpha-olefins, which may be produced via additional multimerization reaction of 1-hexene and/or 1-octene may be also decreased.

After deteriorating the activity of the oligomerization catalyst, a step of separating a product including alpha-olefins may be further included. In this case, the separation may be performed by separating a product including alpha-olefins, other heavy fraction ($C_{10}$ to $C_{40}$ alpha-olefins, etc.), deactivated oligomerization catalyst system, etc. via distillation columns. As described above, in the separating environment of a product, a side reaction, etc. may be restrained due to the deactivation of the oligomerization catalyst system.

In addition, since a separating process is not necessary due to the use of the additive for polymer as the deactivator and the separating process is not performed as described above, after separating 1-hexene and 1-octene from the product the alpha-olefins, the deactivator may be included in a polymer resin product such as polyolefin including polyethylene. Therefore, an additive for polymer for enhancing the physical properties of the polymer resin may not be additionally injected by determining the deactivator according to the physical properties required for the polymer resin product, and economic feasibility and productivity may be improved incidentally.

Multimerization Reaction of Olefin

According to the present disclosure, a method for preparing alpha-olefin oligomer including a step of performing a multimerization reaction of olefin in the presence of an oligomerization catalyst system may be provided.

The multimerization reaction of olefin may generally mean olefin oligomerization, and the multimerization reaction may preferably be a homogeneous liquid phase reaction using an oligomerization catalyst system, a common apparatus and contacting technique in the presence or non-presence of an inert solvent, a slurry reaction in which a catalyst system is not partially or wholly dissolved, a two phase liquid/liquid reaction, or a bulk phase reaction or a gas phase reaction in which an olefin product acts as a main medium. The homogeneous liquid phase reaction is preferable.

The multimerization reaction of olefin may be performed in an optional inert solvent which does not react with a catalyst compound and an activator. Appropriate inert solvent may include benzene, toluene, xylene, cumene, heptane, cyclohexane, methylcyclohexane, methylcyclopentane, hexane, pentane, butane, isobutene, etc., without limitation. In this case, the solvent may be used after removing a small amount of water or air acting as a catalyst poison by treating using a small amount of alkyl aluminum.

The oligomerization reaction of olefin may be performed at a temperature from about 5° C. to about 200° C., and preferably, from about 30° C. to about 150° C. In addition, the oligomerization reaction of olefin may be performed under a pressure from about 1 bar to about 300 bar, and preferably, from about 2 bar to about 150 bar.

Oligomerization Catalyst System

A catalyst system applicable to the method for oligomerization according to an embodiment of the present disclosure may be any catalyst system having a PNP-based ligand compound, without specific limitation. For example, an oligomerization catalyst system including the following ligand compound, transition metal compound and co-catalyst may be applied.

Ligand Compound

The ligand compound may include at least two diphosphine moieties represented by the following Formula 1.

[Formula 1]

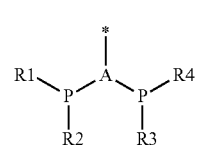

In the above Formula 1, A is N, As or Sb, R1 to R4 are each independently aryl having 6 to 20 carbon atoms or alkylaryl having 7 to 20 carbon atoms, and * is a linker connecting at least two diphosphine moieties.

Further, in the case that the number of the diphosphine moiety represented by the above Formula 1 is two, and A is nitrogen (N), the ligand compound may include a compound represented by the following Formula 1a.

[Formula 1a]

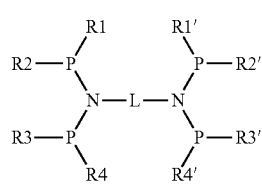

In the above Formula 1a, each of R1 to R4 and R1' to R4' may be selected from the same group of R1 to R4 in Formula 1, and L may be a linker connecting two diphosphine moieties.

The linker L connecting at least two diphosphine moieties may be a hydrocarbyl group having various structures, and the carbon number between the diphosphine moieties for the shortest distance may be from 2 to 8. That is, the hydrocarbyl group is present for the connection between two or more diphosphine moieties, and the carbon number in the hydrocarbyl group for connecting the diphosphine moieties with the shortest distance may be in a range of 2 to 8.

Particularly, the hydrocarbyl linker may be combined with at least one group selected from the group consisting of an aliphatic group having 2 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a hetero aromatic group having 6 to 20 carbon atoms, and may have any structure, without specific limitation only if satisfying the above conditions.

Non-limiting examples of the linker L for connecting at least two groups represented by the above Formula 1 via 2 to 8 carbon atoms may be a compound having an aliphatic group having 2 to 20 carbon atoms (for example, an alkylene group, an alkenylene group, an alkynylene group, or a hetero aliphatic group including a heteroatom in the aliphatic group), an alicyclic group having 2 to 20 carbon atoms (for example, a cycloalkylene group, a cycloalkenylene group, a cycloalkynylene group, or a hetero alicyclic group including a heteroatom in the alicyclic group), or a combined group of the aliphatic (or hetero aliphatic) group and the alicyclic (or hetero alicyclic) group.

Non-limiting examples of the linker may include a hydrocarbyl group represented by the following structures. In the following examples, the diphosphine moiety represented by the above Formula 1 is designated by [A], [A'] or [A''] for convenience, and [A], [A'] or [A''] may be the same or different according to the group selected for R1 to R4.

(i) a compound having a group connecting a plurality of As via two or three carbon atoms:

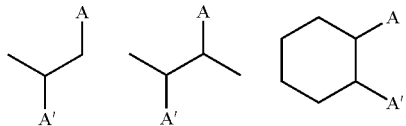

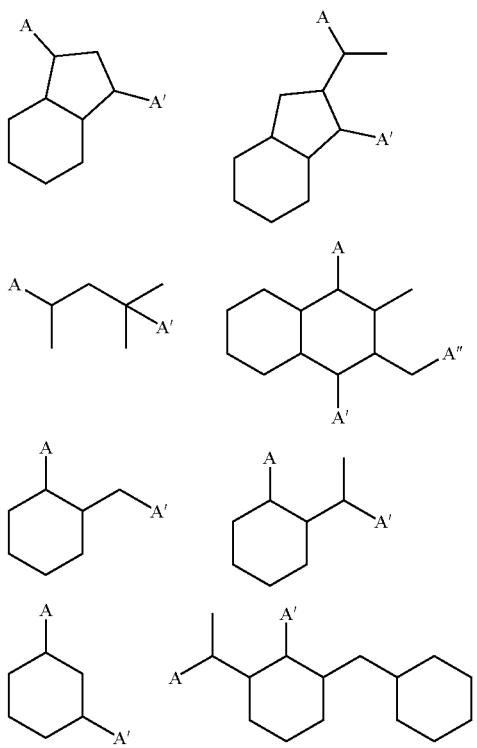

(ii) a compound having a group connecting a plurality of As via four carbon atoms:

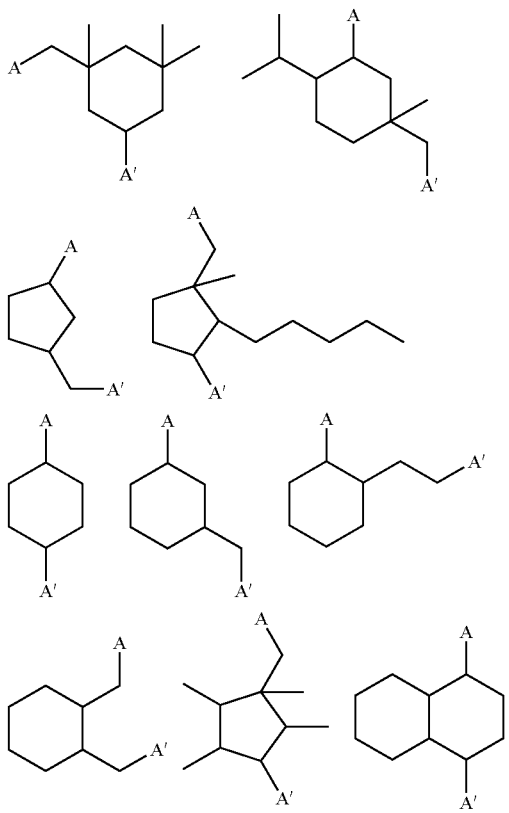

-continued

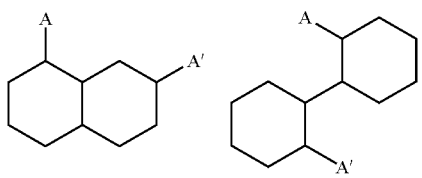

(iii) a compound having a group connecting a plurality of As via five carbon atoms:

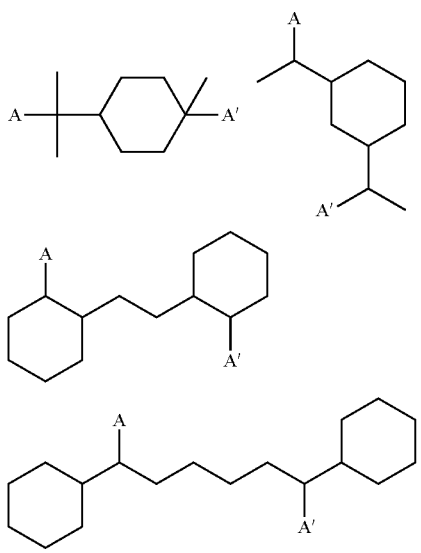

As described above, in the case that at least two diphosphine moieties represented by Formula 1 are connected via four carbon atoms, a connecting group via four carbon atoms may preferably include a flexible aliphatic group for favorable interaction between chromium complexes of the at least two diphosphine moieties.

That is, even though at least two diphosphine moieties represented by Formula 1 are connected via four carbon atoms, in the case that the diphosphine moieties are connected via a group not including an aliphatic group but only including an alicyclic group or an aromatic group such as cyclohexane at positions 1 and 4, interaction may be extremely limited. Accordingly, activity per unit PNP-Cr may be largely decreased, and selectivity for alpha-olefins having a small number of carbon atoms such as 1-hexene and 1-octene may be deteriorated.

Meanwhile, the ligand compound represented by Formula 1 or 1a may be synthesized by the following Reaction 1, without limitation.

[Reaction 1]

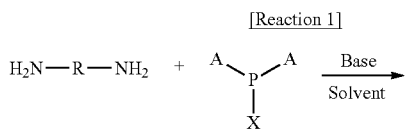

-continued

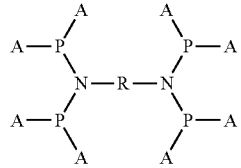

In the above Reaction 1, each A is independently the same or different from each other and is the same as defined for R1 to R4 in Formula 1 or 1a, R is a linker connecting via 2 to 8 carbon atoms and the same as defined in Formula 1 or 1a, and X is halogen.

According to another embodiment of the present disclosure, the ligand compound may include a compound represented by the following Formula 2.

[Formula 2]

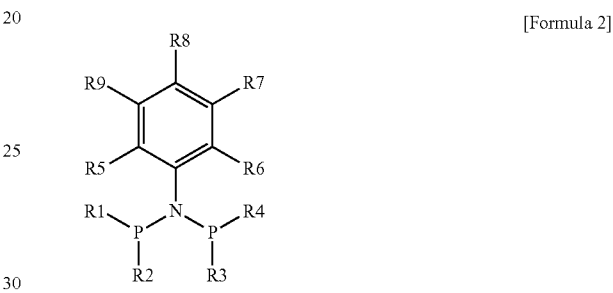

In Formula 2, R1 to R4 are each independently aryl having 6 to 20 carbon atoms or alkylaryl having 7 to 20 carbon atoms, and R5 may be alkyl having 1 to 20 carbon atoms.

In the case that R5 is methyl, R6 may be a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 may be alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 may be each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

As described above, the ligand compound represented by Formula 2 may be, for example, a compound obtained by substituting at carbon atoms of positions 2 and 6 in an aniline compound with R5 and R6, and the properties of the ligand compound and the oligomerization catalyst system including the same may be changed according to the substituent at the carbon atoms of positions 2 and 6.

In the case where a methyl group is substituted at the carbon atom of position 2, a group different from the substituent at position 2 may be substituted at the carbon atom of position 6 to attain an asymmetric structure.

As non-limiting examples, a linear group of an alkyl group, an alkenyl group, a heteroalkyl group, a heteroalkenyl group, or the heteryl group thereof having 2 or 3 carbon atoms may be substituted; or an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 4 to 20 carbon atoms may be substituted.

In addition, a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteroaryl group thereof having 6 to 20 carbon atoms may be substituted; or an alkylaryl group, a heteroalkylaryl group, or the heteryl group thereof having 7 to 20 carbon atoms may be substituted.

In addition, in the case where an alkyl group having 2 to 20 carbon atoms is substituted at the carbon atom of position 2, a substituent same as or different from the substituent at position 2 may be substituted at the carbon atom of position 6.

As non-limiting examples, an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 2 to 20 carbon atoms may be substituted; a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

Due to the structural characteristics of the substituent groups for the aniline group, in the catalyst system including the ligand compound, PNP-Cr may easily interact according to various conditions such as electronic or steric circumstances around a transition metal, and the high activity of an oligomerization reaction may be illustrated. Further, high selectivity particularly for 1-hexene, 1-octene, etc. may be illustrated, and the amount of an 1-hexene isomer which may induce large affects to a product during oligomerization may be largely decreased. Accordingly and incidentally, energy may be saved, because a separating process may become unnecessary according to the increase of 1-hexene and the decrease of the 1-hexene isomer.

The ligand compound may be synthesized by the following Reaction 2, without limitation.

[Reaction 2]

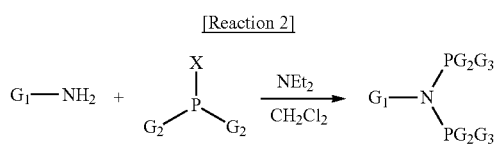

In the above Reaction 2, G1 may be a phenyl group having R5 to R9 in Formula 2, each of G2 and G3 may be R1 to R4 in Formula 3, and X may be halogen.

Reaction 2 is a general reaction for synthesizing a ligand compound represented by Formula 3 and may be a reaction for producing diphosphinoamine via the reaction of an amine and phosphine. That is, in the reaction, the amine as a nucleophile may push a leaving group represented by X in the phosphine for substitution. X may be any functional group which may be easily separated and stabilized, without limitation. Typically, halogens such as Cl, Br or I may be used.

Ligand Compound and Transition Metal Compound

Such a selective olefin oligomerization reaction is closely concerned with a catalyst system used. The catalyst system used for the oligomerization reaction of olefin includes a transition metal compound acting as a main catalyst and a co-catalyst. In this case, according to the chemical structure of the ligand, the structure of an active catalyst may be changed, and olefin selectivity, activity or the amount of by-products may be changed.

The transition metal compound in the oligomerization catalyst system according to an embodiment of the present disclosure acts as a main catalyst and may have a state making a coordination bond with the ligand compound as described above.

Particularly, the transition metal compound and the ligand compound including at least two diphosphine moieties represented by the above Formula 1 may make a coordination bond as represented in the following Formula 1-1.

[Formula 1-1]

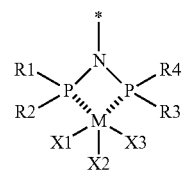

In the above Formula 1-1, R1 to R4 and are the same as defined in Formula 1, M may be a transition metal, and preferably, Cr, and X1 to X3 are each independently H, F, Cl, Br, I, alkyl, alkenyl, arylalkyl, heteroalkyl, heteroalkenyl or heteroarylalkyl having 1 to 6 carbon atoms, or halogen.

In addition, the transition metal compound and the ligand compound represented by Formula 1a may make a coordination bond as shown in the following Formula 2a-1.

[Formula 1a-1]

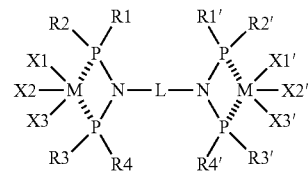

In Formula 1a-1, R1 to R4, X1 to X3 and M are the same as defined in Formula 1-1, R1' to R4' and X1' to X3' are also the same as R1 to R4 and X1 to X3.

The transition metal compound and the ligand compound represented by Formula 3 may make a coordination bond as shown in the following Formula 2-1.

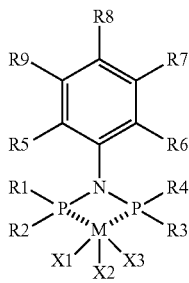

[Formula 2-1]

In Formula 2-1, X1 to X3 and M are the same as defined in Formula 1-1, and R1 to R9 are the same as defined in Formula 2.

Particularly, the transition metal compound may include an organochromium compound, and the organochromium compound may be at least one selected from the group consisting of chromium(III)acetylacetonate, trichlorochromiumtristetrahydrofuran, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate and chromium(III)acetatehydroxide.

Co-Catalyst

The co-catalyst is an organometallic compound including a metal in group 13 and may be generally any one which may be used for multimerizing olefin in the presence of a transition metal compound catalyst, without specific limitation. Particularly, the co-catalyst may be at least one selected from the group consisting of the compounds represented by the following Formulae 3 to 5.

[Formula 3]

In the above Formula 3, each $R_5$ is the same or different from each other and is independently a halogen radical, a hydrocarbyl radical having 1 to 20 carbon atoms, or a halogen substituted hydrocarbyl radical having 1 to 20 carbon atoms, and c is an integer of at least 2.

[Formula 4]

In the above Formula 4, D is aluminum or boron, each $R_6$ is the same or different from each other and is independently hydrogen or halogen, hydrocarbyl having 1 to 20 carbon atoms, or halogen substituted hydrocarbyl having 1 to 20 carbon atoms.

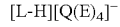

[Formula 5]

In the above Formula 5, L is a neutral Lewis acid, [L-H]$^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

The compound represented by Formula 3 may be modified methyl aluminoxane (MAO), methyl aluminoxane (MAO), ethyl aluminoxane, isobutyl aluminoxane, butyl aluminoxane, etc.

The alkyl metal compound represented by the above Formula 4 may include, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc.

Examples of the compound represented by the above Formula 5 includes, for example, triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, etc.

The co-catalyst of the oligomerization catalyst system according to an embodiment may preferably include aluminoxane, and more preferably, methyl aluminoxane (MAO) or modified methyl aluminoxane (MMAO) may be used.

The oligomerization catalyst system may include the ligand compound:the transition metal compound:the co-catalyst in a molar ratio from about 0.5:1:1 to about 10:1:10,000, and preferably, from about 0.5:1:100 to about 5:1:3,000 to increase selectivity for linear alpha-olefins and to increase the activity of a multimerization reaction. However, the oligomerization catalyst system according to the present disclosure is not limited thereto.

In the catalyst system including the ligand compound, the transition metal compound and the co-catalyst, the three components of the catalyst system may be added simultaneously or one by one in an optional order to an optionally appropriate solvent in the presence or non-presence of a monomer to produce a catalyst with activity. An appropriate solvent may include heptane, toluene, cyclohexane, methylcyclohexane, 1-hexene, diethyl ether, tetrahydrofuran, acetonitrile, dichloromethane, chloroform, chlorobenzene, methanol, acetone, etc., without limitation.

EXAMPLES

Hereinafter, examples of the present invention will be explained in detail so that a person skilled in the art may easily perform. However, the present invention may be embodied in various modifications and is not limited to the examples herein.

Preparation Example: Multimerization Reaction of Olefin

1) Preparation of Catalyst Solution

Under an argon gas atmosphere, Cr(acac)$_3$ (17.5 mg, 0.05 mmol) and a certain ligand compound (1.1 eq. to Cr) were added to a flask, and 100 ml of methylcyclohexane was added thereto, followed by stirring to obtain a 0.5 mM (to Cr) catalyst solution.

2) Multimerization Reaction of Olefin

A parr reactor having a volume of 600 ml was prepared and a vacuum state was made at 120 for 2 hours. Then, the inner portion of the reactor was replaced with argon, and the temperature was decreased to 60. After that, 140 g of methylcyclohexane and 1.6 ml of MMAO (8.6 wt %, isoheptane solution) (Al/Cr=1,200) were injected, and 5 ml (2.5 µmol) of the 0.5 mM catalyst solution was injected to the reactor. The valve of an ethylene line adjusted to 60 bar was opened to fill up the reactor with ethylene, followed by stirring in 500 rpm for 15 minutes.

3) Sample Collection

The valve of an ethylene line was closed, and the reactor was cooled to 0 using a dry ice/acetone bath, unreacted ethylene was slowly ventilated, and 1 ml of nonane (GC internal standard) was injected. After that, a small amount of the liquid portion of the reactor was collected as a sample and quenched with water. An organic layer was filtered using a PFTE syringe filter, and GC analysis was conducted.

Example 1

The sample of the preparation example was injected to a reactor filled with an argon gas, and stirring and ventilation were repeated to remove residual ethylene at the most. Then, bis(2-hydroxyethyl)pentadecylamine (Atmer 163) which is a kind of an antistatic agent (polymer additive) was injected as a deactivator, followed by stirring for 10 minutes. Then, in order to form environment for separating a product (for example, distillation), thermal hysteresis was applied by heating at 150° C. for 3.5 hours. The temperature was decreased to room temperature (about 25° C.), and GC analysis was conducted.

Example 2

GC analysis was conducted after applying thermal hysteresis by the same method described in Example 1 except for injecting a mixture solution of decanol and Atmer 163 instead of Atmer 163 as the deactivator.

Example 3

GC analysis was conducted after applying thermal hysteresis by the same method described in Example 1 except for injecting triisopropanolamine (TIPA) instead of Atmer 163 as the deactivator.

Example 4

GC analysis was conducted after applying thermal hysteresis by the same method described in Example 1 except for injecting quadrol(N,N,N,N-tetrakis(2-hydroxypropyl)-ethylenediamine) instead of Atmer 163 as the deactivator.

Comparative Example 1

GC analysis was conducted after applying thermal hysteresis by the same method described in Example 1 except for not injecting the deactivator.

Comparative Example 2

GC analysis was conducted after applying thermal hysteresis by the same method described in Example 1 except for injecting decanol instead of Atmer 163 as the deactivator.

Experimental Example 1: Evaluation According to the Kind of Deactivator

In the following Table 1, the results obtained via the GC analysis of the products from an olefin multimerization reaction (preparation example) and the results obtained via the GC analysis of the products after injecting the deactivator (examples and comparative examples) are compared, and the increase or decrease of each compound is represented by %.

TABLE 1

| | Deactivator | 1-$C_6$ | iso-$C_6$ | 1-$C_8$ | iso-$C_8$ | $C_{10}$-$C_{40}$ | PE Wax (g) |
|---|---|---|---|---|---|---|---|
| Example 1 | Atmer 163 | 100% | 99% | 97% | 139% | 101% | 1.7 |
| Example 2 | Atmer 163 + decanol | 99% | 99% | 99% | 102% | 104% | 0.4 |
| Example 3 | TIPA | 105% | 104% | 99% | 103% | 101% | — |
| Example 4 | Quadrol | 99% | 99% | 100% | 104% | 102% | — |
| Comparative Example 1 | X | 95% | 117% | 97% | 260% | 112% | 1.9 |
| Comparative Example 2 | Decanol | 97% | 99% | 100% | 101% | 105% | 1.2 |

Referring to Table 1, for Examples 1 to 4 using the additive for polymer, the content of alpha-olefins with a long chain, that is, $C_{10}$ to $C_{40}$ and the content of a $C_6$ isomer are similar to or greater when compared to that in Comparative Examples 1 and 2 using the conventional deactivator. Particularly, for solid alpha-olefins ($C_{10}$-$C_{40}$), the content was decreased by about 1-5% for the examples when compared to that for the comparative examples, and the content of the $C_6$ isomer was decreased further by about 20%.

From the results, in the case that the activity of the oligomerization catalyst system is deteriorated using the oligomerization method according to the present disclosure, the side reactions such as additional multimerization reaction, the isomerization reaction, etc. of the product may be effectively prevented. Since the material used as the additive for polymer was used as the deactivator, a separating process is not required. Therefore, the deactivation of the oligomerization catalyst system according to the present disclosure is preferable when compared to a case of not using a deactivator and a case of using the conventional deactivator.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:

1. A method for oligomerizing an olefin using an oligomerization catalyst system, the method comprising:
   injecting a deactivator into a product mixture of an oligomerization reaction of an olefin to deteriorate activity of the oligomerization catalyst system, and
   separating the product mixture into an alpha-olefin product and a polymer resin product after deteriorating the activity of the oligomerization catalyst system,
   wherein the polymer resin product contains a mixture of polyethylene and the deactivator,
   wherein the deactivator comprises an additive including at least one functional group selected from the group consisting of a hydroxyl group, an amine group and an amide group,
   wherein the additive comprises at least one selected from the group consisting of an antistatic agent, an antioxidant, a lubricant, a stabilizer, and a phase transfer catalyst, and
   wherein the method does not include separating the deactivator from the polymer resin product.

2. The method for oligomerizing an olefin of claim 1, wherein a molar ratio of the oligomerization catalyst system to the deactivator is from 1:1 to 1:100.

3. The method for oligomerizing an olefin of claim 1, wherein the additive comprises the antistatic agent, and wherein the antistatic agent comprises at least one selected from the group consisting of bis(2-hydroxyethyl)pentadecylamine, an ethoxylated fatty amine having 12 to 18 carbon atoms, glycerol monostearate, erucamide, stearamide, oleamide and benenamide.

4. The method for oligomerizing an olefin of claim 1, wherein the additive comprises the antioxidant, and wherein the antioxidant comprises butylated hydroxytoluene (BHT).

5. The method for oligomerizing an olefin of claim 1, wherein the additive comprises the lubricant, and wherein the lubricant comprises at least one selected from the group consisting of erucamide, stearamide, oleamide, benenamide, an ethoxylated fatty amine having 12 to 18 carbon atoms and glycerol monostearate.

6. The method for oligomerizing an olefin of claim 1, wherein the additive comprises the stabilizer, and wherein the stabilizer comprises triisopropanolamine (TIPA), quadrol(N,N,N,N-tetrakis(2-hydroxypropyl)-ethylenediamine) or a mixture thereof.

7. The method for oligomerizing an olefin of claim 1, wherein the deactivator comprises a light stabilizer, and wherein the light stabilizer comprises a benzotriazole-based compound.

8. The method for oligomerizing an olefin of claim 1, wherein the additive comprises the phase transfer catalyst, and wherein the phase transfer catalyst comprises tricaprylmethylammonium chlorine.

9. The method for oligomerizing an olefin of claim 1, wherein the oligomerization catalyst system comprises a diphosphine-based ligand compound; a transition metal compound; and a co-catalyst.

10. The method for oligomerizing an olefin of claim 9, wherein the transition metal compound comprises an organic chromium compound, and the organic chromium compound comprises at least one selected from the group consisting of chromium(III) acetyl acetonate, trichloro chromium tris tetrahydrofuran, chromium(III)-2-ethylhexanoate, chromium(III) tris (2,2,6,6-tetramethyl-3,5-heptanedionate), chromium(III) benzoyl acetonate, chromium(III) hexafluoro-2,4-pentanedionate, and chromium(III) acetate hydroxide.

11. The method for oligomerizing an olefin of claim 9, wherein the diphosphine-based ligand compound comprises at least two diphosphine moieties represented by Formula 1, or a compound represented by Formula 2:

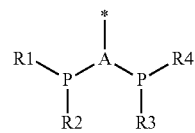

[Formula 1]

wherein in Formula 1, A is N, As or Sb; R1 to R4 are each independently aryl groups having 6 to 20 carbon atoms or alkylaryl groups having 7 to 20 carbon atoms, and * is a linker connecting the at least two diphosphine moieties;

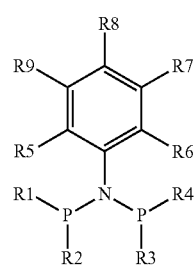

[Formula 2]

wherein in Formula 2,
R1 to R4 are the same as defined in Formula 1, and R5 is an alkyl group having 1 to 20 carbon atoms,
with the proviso that when R5 is a methyl group, R6 is (i) a linear alkyl group, a linear alkenyl group, a linear heteroalkyl group, a linear heteroalkenyl group, or a heteryl group thereof having 2 or 3 carbon atoms; (ii) an alkyl group, an alkenyl group, an arylalkyl group, an arylalkenyl group, a heteroalkyl group, a heteroalkenyl group, a heteroarylalkyl group, a heteroarylalkenyl group, or a heteryl group thereof having 4 to 20 carbon atoms; (iii) a cycloalkyl group, a cycloalkenyl group, an arylcycloalkyl group, an arylcycloalkenyl group, a heteroarylcycloalkyl group, a heteroarylcycloalkenyl group, or a heteryl group thereof having 3 to 20 carbon atoms; (iv) an aryl group, a heteroaryl group, or a heteryl group thereof having 6 to 20 carbon atoms; or (v) an alkylaryl group, a heteroalkylaryl group, or a heteryl group thereof having 7 to 20 carbon atoms;
with the proviso that when R5 is an alkyl group having 2 to 20 carbon atoms, R6 is: (i) an alkyl group, an alkenyl group, an arylalkyl group, an arylalkenyl group, a heteroalkyl group, a heteroalkenyl group, a heteroarylalkyl group, a heteroarylalkenyl group, or a heteryl group thereof having 2 to 20 carbon atoms; (ii) a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or a heteryl group thereof having 3 to 20 carbon atoms; an aryl group, a heteroaryl group, or a heteryl group thereof having 6 to 20 carbon atoms; or (iv) an alkylaryl group, a heteroalkylaryl group, or a heteryl group thereof having 7 to 20 carbon atoms; and R7 to R9 are each independently: (i) hydrogen; (ii) an alkyl group, an alkenyl group, an arylalkyl group, or an arylalkenyl group having 1 to 20 carbon atoms; (iii) a cycloalkyl group, a cycloalkenyl group, an arylcycloalkyl group, or an arylcycloalkenyl group having 3 to 20 carbon atoms; (iv) an aryl group having 6 to 20 carbon atoms; or (v) an alkylaryl group having 7 to 20 carbon atoms.

12. The method for oligomerizing an olefin of claim 11, wherein the linker in Formula 1 is selected from the group consisting of an aliphatic group having 1 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a heteroaromatic group having 6 to 20 carbon atoms.

* * * * *